(12) United States Patent
Lou et al.

(10) Patent No.: US 12,639,809 B2
(45) Date of Patent: May 26, 2026

(54) QUALITY ASSURANCE WORKFLOWS FOR LOW-FIELD MRI PROSTATE DIAGNOSTIC SYSTEMS

(71) Applicant: SIEMENS HEALTHINEERS AG, Forchheim (DE)

(72) Inventors: Bin Lou, Princeton Junction, NJ (US); Ali Kamen, Skillman, NJ (US); Boris Mailhe, Plainsboro, NJ (US); Mariappan S. Nadar, Plainsboro, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 470 days.

(21) Appl. No.: 18/063,116

(22) Filed: Dec. 8, 2022

(65) Prior Publication Data

US 2023/0252623 A1    Aug. 10, 2023

Related U.S. Application Data

(60) Provisional application No. 63/267,735, filed on Feb. 9, 2022.

(51) Int. Cl.
*G06T 7/00* (2017.01)
*G06V 10/77* (2022.01)
(Continued)

(52) U.S. Cl.
CPC ........ *G06T 7/0012* (2013.01); *G06V 10/7715* (2022.01); *G06V 10/7753* (2022.01);
(Continued)

(58) Field of Classification Search
CPC ........... G06V 10/77–772; G06V 10/96; G06V 2201/03; G06V 10/7753; G06V 10/82;
(Continued)

(56) References Cited

U.S. PATENT DOCUMENTS

| | | | |
|---|---|---|---|
| 2007/0258559 A1* | 11/2007 | Hur ........................ | A61B 6/583 |
| | | | 378/109 |
| 2019/0150857 A1* | 5/2019 | Nye ........................ | G16H 30/40 |

(Continued)

FOREIGN PATENT DOCUMENTS

| | | | |
|---|---|---|---|
| CN | 201910940600 | * | 4/2020 |
| WO | WO-2022203592 A1 | * | 9/2022 |

OTHER PUBLICATIONS

Belton, Niamh, Aonghus Lawlor, and Kathleen M. Curran. "Semi-supervised siamese network for identifying bad data in medical imaging datasets." arXiv preprint arXiv:2108.07130 (2021). (Year: 2021).*

(Continued)

*Primary Examiner* — Gregory A Morse
*Assistant Examiner* — Stefano Anthony Dardano

(57) ABSTRACT

Systems and methods for performing a quality assessment of a medical imaging analysis task are provided. At least one low-field MRI (magnetic resonance imaging) quality assurance imaging data of the patient is received. A quality assessment of a medical imaging analysis task is performed based on the at least one low-field MRI quality assurance imaging data using one or more machine learning based networks. Results of the quality assessment are output.

17 Claims, 7 Drawing Sheets

300

(51) Int. Cl.
| | |
|---|---|
| *G06V 10/774* | (2022.01) |
| *G06V 10/82* | (2022.01) |
| *G06V 10/96* | (2022.01) |
| *G16H 50/20* | (2018.01) |

(52) U.S. Cl.
CPC .............. *G06V 10/82* (2022.01); *G06V 10/96* (2022.01); *G16H 50/20* (2018.01); *G06T 2207/10088* (2013.01); *G06T 2207/30081* (2013.01)

(58) Field of Classification Search
CPC .... G06V 2201/031; G06T 2207/30168; G06T 7/0002; G06T 7/0012; G06T 2207/20081; G06T 2207/20084; G06T 9/002; G06T 2207/10088; G06T 2207/30081; G06T 2210/41; G01N 33/57434; G16H 50/20; G16H 50/30; G16H 30/40; G16H 50/70
See application file for complete search history.

(56) References Cited

U.S. PATENT DOCUMENTS

| | | | | |
|---|---|---|---|---|
| 2021/0321968 A1* | 10/2021 | Sun | .......................... | A61B 6/03 |
| 2022/0202499 A1* | 6/2022 | Zhang | ............. | G01R 33/56509 |
| 2022/0405927 A1* | 12/2022 | Villard | ................. | A61B 3/0008 |
| 2024/0350109 A1* | 10/2024 | Sevenster | .............. | G16H 30/40 |

OTHER PUBLICATIONS

U.S. Appl. No. 17/648,135, filed Jan. 17, 2022, 42 pgs.

\* cited by examiner

Figure 1:
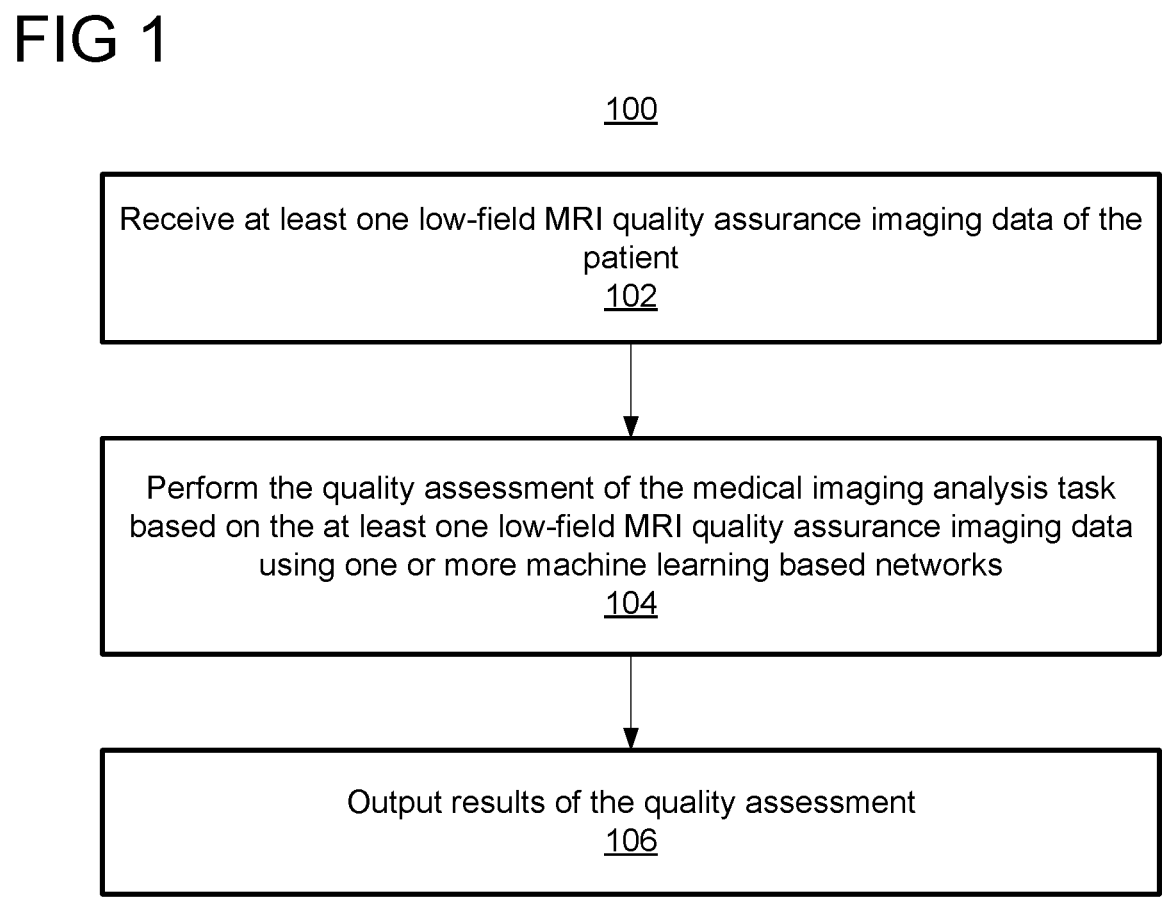

```
Receive at least one low-field MRI quality assurance imaging data of the
patient
102
```

```
Perform the quality assessment of the medical imaging analysis task
based on the at least one low-field MRI quality assurance imaging data
using one or more machine learning based networks
104
```

```
Output results of the quality assessment
106
```

600

QUALITY ASSURANCE WORKFLOWS FOR LOW-FIELD MRI PROSTATE DIAGNOSTIC SYSTEMS

CROSS-REFERENCE TO RELATED APPLICATIONS

This application claims the benefit of U.S. Provisional Application No. 63/267,735, filed Feb. 9, 2022, the disclosure of which is herein incorporated by reference in its entirety.

TECHNICAL FIELD

The present invention relates generally to automatic low-field MRI (magnetic resonance imaging) diagnostic systems, and in particular to quality assurance workflows for low-field MRI prostate cancer diagnostic systems.

BACKGROUND

Low-field MRI (magnetic resonance imaging) systems offer low-cost imaging using relatively low strength MR fields as compared to high-field MRI systems often used for diagnostic imaging. Such low-field MRI systems have a smaller footprint and do not need to be magnetically shielded, and therefore may be installed at more publicly accessible areas such as, e.g., pharmacies or medical clinics. However, due to the low strength MR fields, such low-field MRI systems generate low-field MRI images with relatively lower quality that are not sufficient for radiologists to read. Recently, various methods have been proposed for the automatic analysis of low-field MRI images for, e.g., the detection of prostate cancer. However, patient movement and image artifacts may result in low-field MRI images of even further degraded quality, which may result in inaccuracy of the automatic analysis of the low-field MRI images.

BRIEF SUMMARY OF THE INVENTION

In accordance with one or more embodiments, systems and methods for quality assessment of low-field MRI quality assurance images of a patient are provided. The results of the quality assessment may be utilized to, for example, notify the patient that results of an automatic assessment of low-field MRI diagnostic images may be inaccurate and that the patient should reacquire the low-field MRI diagnostic images.

Advantageously, the quality assessment in accordance with embodiments described herein enables an automatic workflow for the automatic analysis of low-field MRI diagnostic images that may be implemented in a pharmacy, a medical clinic, or other publicly accessible areas without requiring guidance, review, or intervention by a radiologist or other clinician.

Systems and methods for performing a quality assessment of a medical imaging analysis task are provided. At least one low-field MRI (magnetic resonance imaging) quality assurance imaging data of the patient is received. A quality assessment of a medical imaging analysis task is performed based on the at least one low-field MRI quality assurance imaging data using one or more machine learning based networks. Results of the quality assessment are output.

In one embodiment, performing the quality assessment of the medical imaging analysis task comprises detecting at least one of an incorrect positioning of the patient or image artifacts based on the at least one low-field MRI quality assurance imaging data using the one or more machine learning based networks. In one embodiment, the one or more machine learning based networks are trained with a supervised approach using labeled training data to classify the at least one low-field MRI quality assurance imaging data as being one of high quality or low quality. In another embodiment, the one or more machine learning based networks are trained using with an unsupervised approach using unlabeled training data to determine whether the at least one low-field MRI quality assurance imaging data is out of distribution of the unlabeled training data.

In one embodiment, the medical imaging analysis task is performed based on one or more low-field MRI diagnostic imaging data acquired from the patient. The at least one low-field MRI quality assurance imaging data comprises first low-field MRI quality assurance imaging data acquired prior to the acquisition of the one or more low-field MRI diagnostic imaging data and second low-field MRI quality assurance imaging data acquired after the acquisition of the one or more low-field MRI diagnostic imaging data. The quality assessment of the medical imaging analysis task is performed based on the first low-field MRI quality assurance imaging data and the second low-field MRI quality assurance imaging data.

In one embodiment, the quality assessment of the medical imaging analysis task may be performed by extracting a first set of features from the first low-field MRI quality assurance imaging data using the one or more machine learning based networks, extracting a second set of features from the second low-field MRI quality assurance imaging data using the one or more machine learning based networks, and computing a distance between the first set of features and the second set of features. In one embodiment, the one or more machine learning based networks comprise a Siamese neural network and the first set of features is extracted from the first low-field MRI quality assurance imaging data using a first subnetwork of the Siamese neural network and the second set of features is extracted from the second low-field MRI quality assurance imaging data using a second subnetwork of the Siamese neural network.

In one embodiment, one or more additional low-field MRI quality assurance imaging data of the patient acquired between the first low-field MRI quality assurance imaging data and the second low-field MRI quality assurance imaging data are received. The quality assessment is performed based on the first low-field MRI quality assurance imaging data, the second low-field MRI quality assurance imaging data, and the one or more additional low-field MRI quality assurance imaging data.

In one embodiment, the at least one low-field MRI quality assurance imaging data comprises at least one of raw k-space data, MR fingerprinting data, or reconstructed images.

These and other advantages of the invention will be apparent to those of ordinary skill in the art by reference to the following detailed description and the accompanying drawings.

BRIEF DESCRIPTION OF THE DRAWINGS

FIG. 1 shows a method for performing a quality assessment of a medical imaging analysis task, in accordance with one or more embodiments;

3

Figure 3:
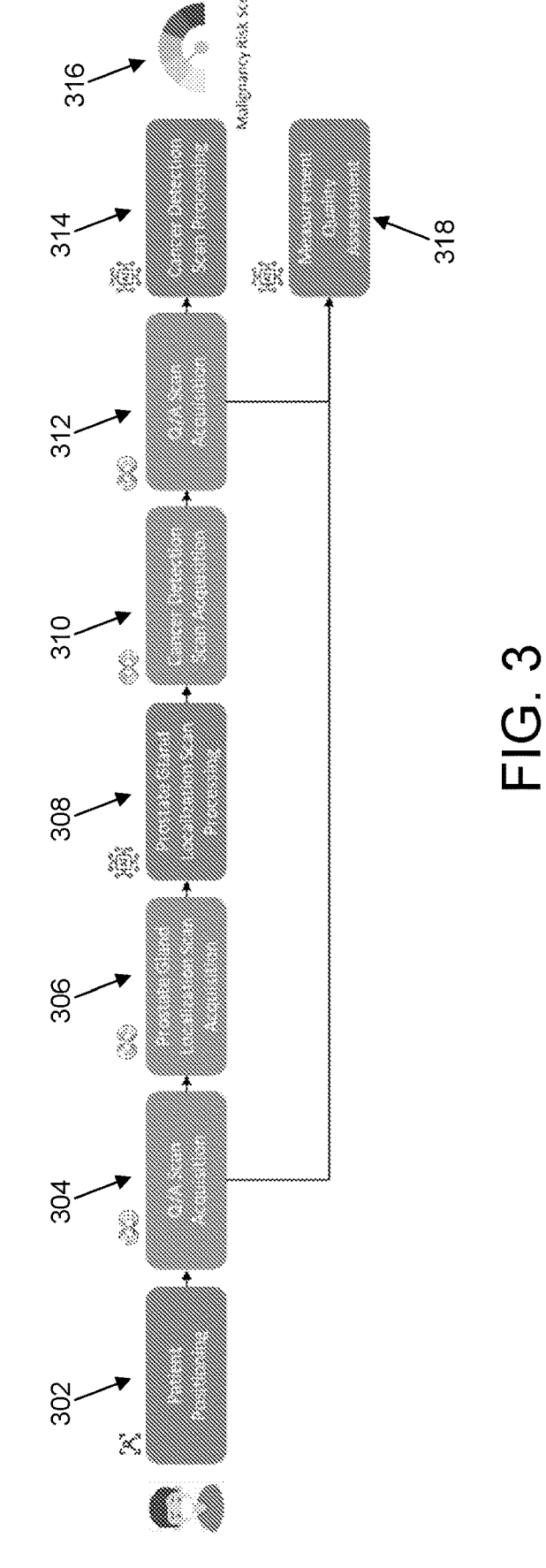
Figure 4:
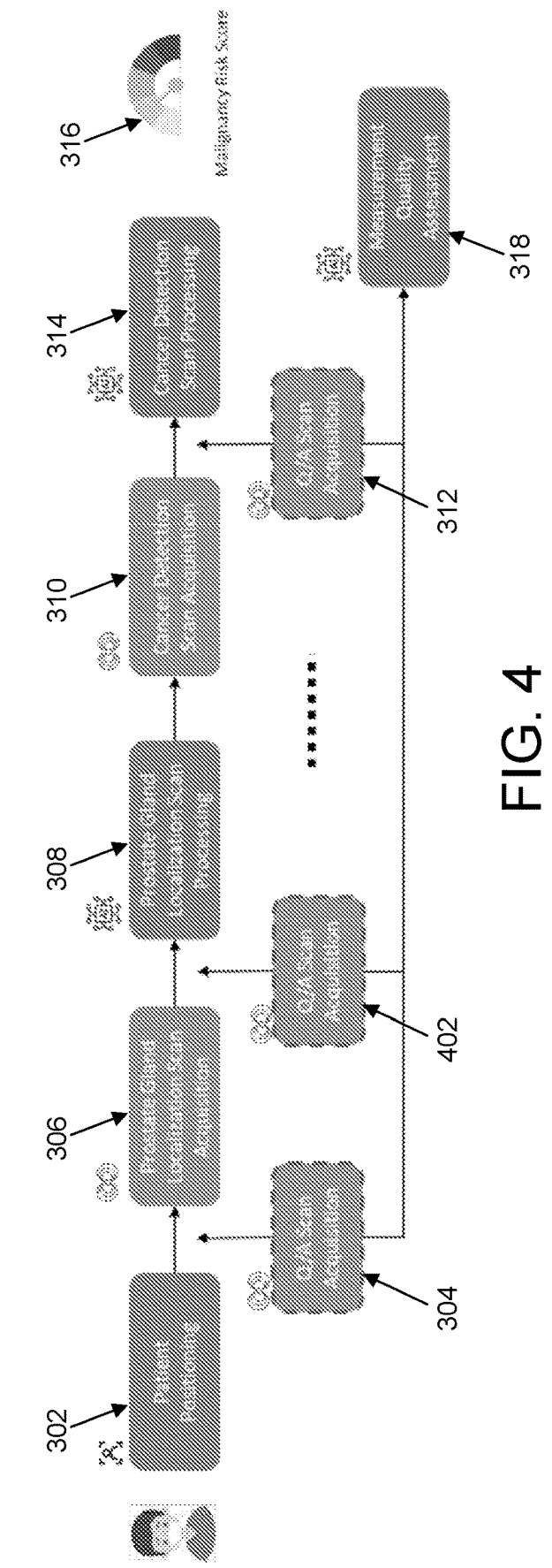
Figure 5:
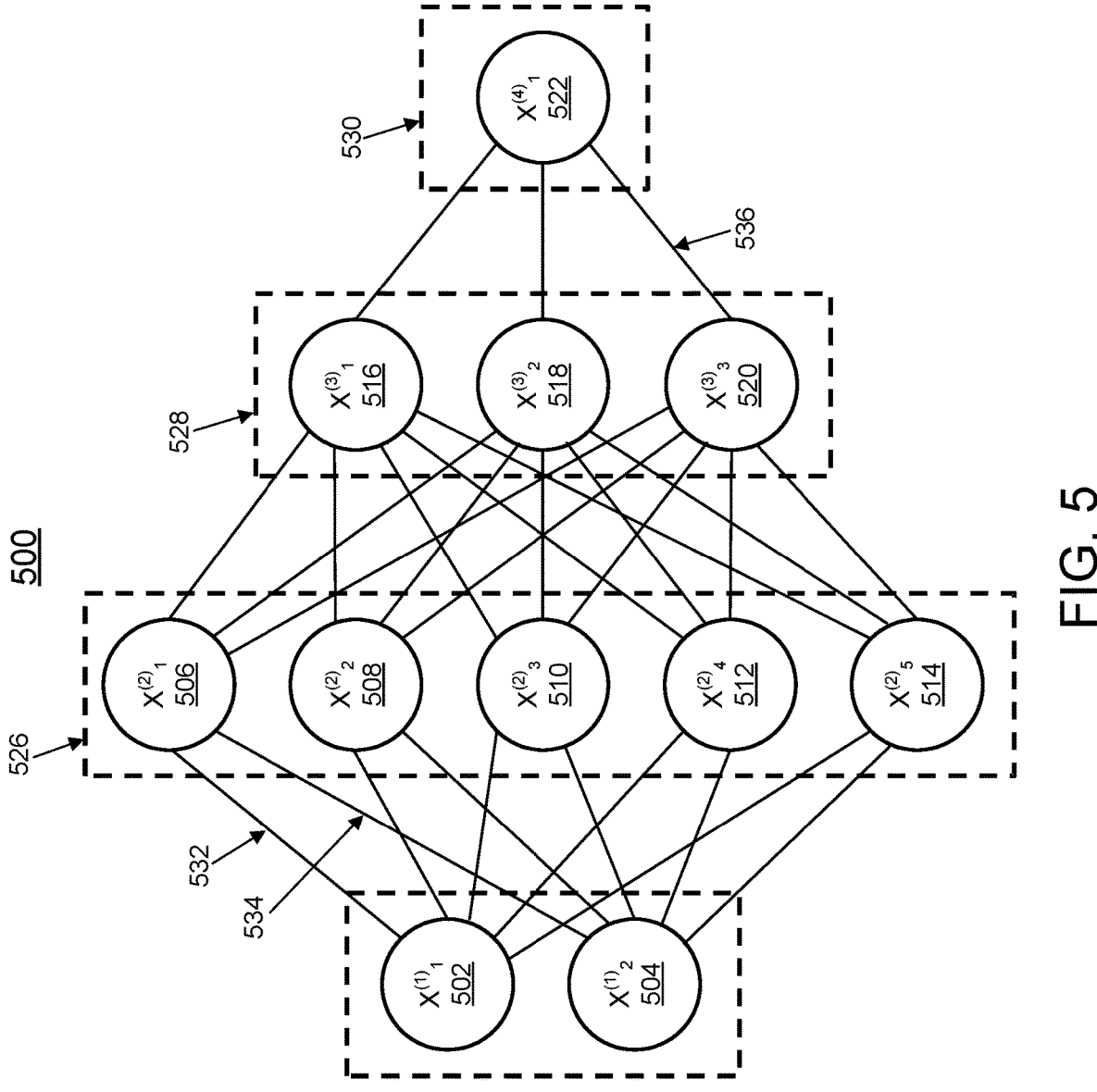
Figure 6:
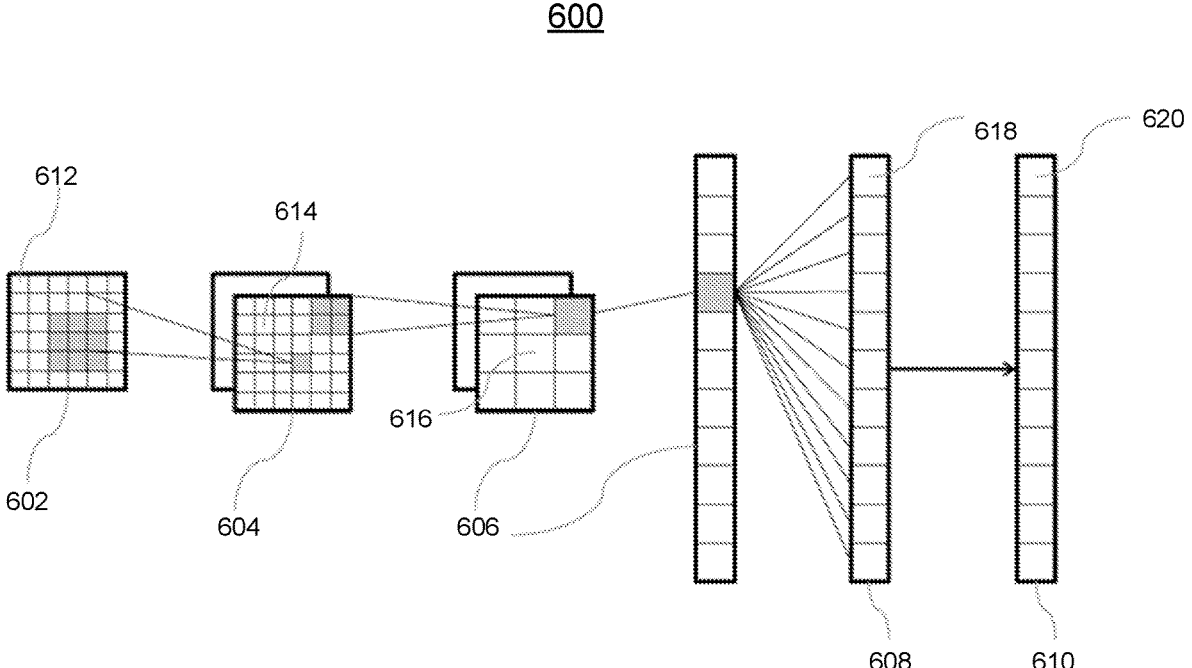
Figure 7:
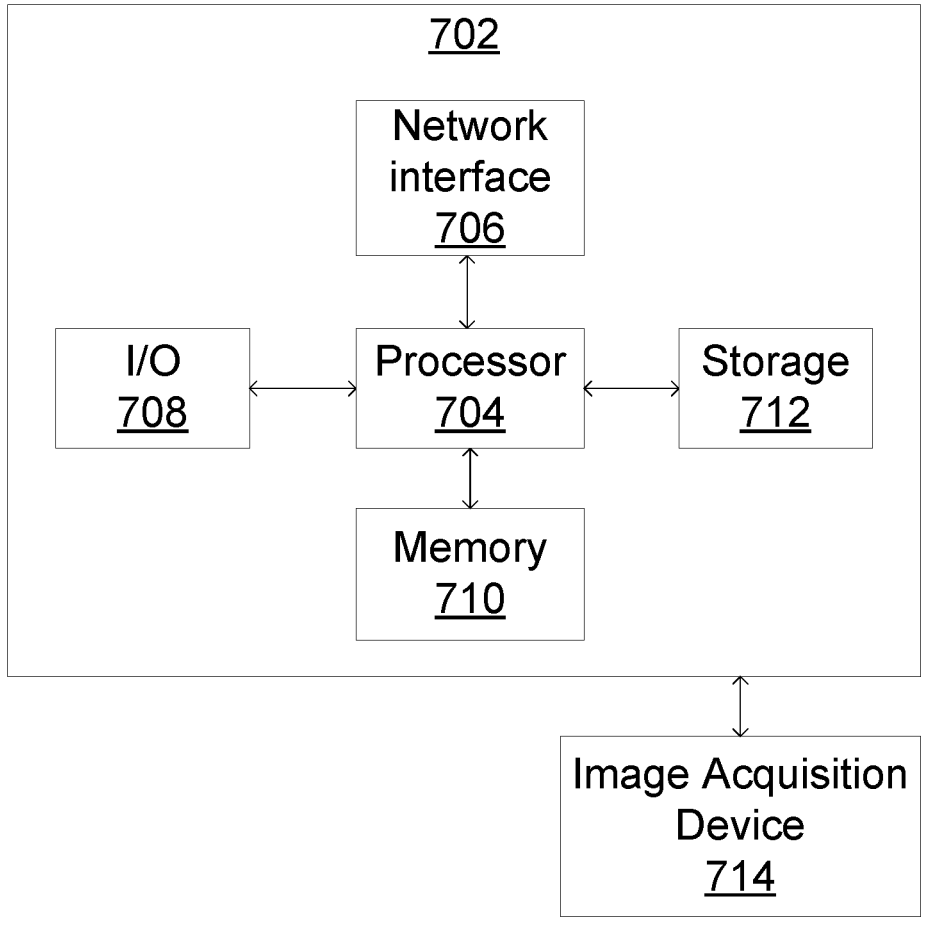

FIG. 3 shows a workflow for the automatic detection of prostate cancer using a low-field MRI diagnostic system, in accordance with one or more embodiments;

FIG. 4 shows a workflow for the automatic detection of prostate cancer using a low-field MRI diagnostic system based on additional low-field MRI quality assurance imaging data, in accordance with one or more embodiments;

FIG. 5 shows an exemplary artificial neural network that may be used to implement one or more embodiments;

FIG. 6 shows a convolutional neural network that may be used to implement one or more embodiments; and FIG. 7 shows a high-level block diagram of a computer that may be used to implement one or more embodiments.

DETAILED DESCRIPTION

The present invention generally relates to methods and systems for quality assurance workflows for low-field MRI prostate diagnostic systems. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Embodiments disclosed herein will be described with reference to the figures, where like reference numerals represent the same or similar elements.

Embodiments disclosed herein provide for quality assessment of a medical imaging analysis task based on one or more low-field MRI quality assurance imaging data acquired for a patient. The results of the quality assessment provide for an indication of the accuracy of the medical imaging analysis task. Advantageously, embodiments described herein may be implemented in a low-field MRI diagnostic system to enable a fully automatic workflow for the automatic performance of the medical imaging analysis task without requiring guidance, review, or intervention by a radiologist or other clinician. For example, the low-field MRI diagnostic system may be installed as a kiosk at a publicly accessible area, such as, e.g., a pharmacy or a medical clinic, to enable the patient to acquire low-field MRI diagnostic images him or herself for the automatic analysis (e.g., detection of prostate cancer) of the low-field MRI diagnostic images. Where results of the quality assessment indicate that the accuracy of the automatic analysis may be low, the patient may be notified and prompted to reacquire the low-field MRI diagnostic images to repeat the automatic analysis on the reacquired low-field MRI diagnostic images.

FIG. 1 shows a method 100 for performing a quality assessment of a medical imaging analysis task, where the medical imaging analysis task is performed based on one or more low-field MRI diagnostic medical images of a patient, in accordance with one or more embodiments. The steps of method 100 may be performed by one or more suitable computing devices, such as, e.g., computer 702 of FIG. 7.

At step 102 of FIG. 1, at least one low-field MRI quality assurance imaging data of a patient is received. The at least one low-field MRI quality assurance imaging data is acquired from a low-field MRI imaging device. The low-field MRI imaging device is an MRI imaging device that utilizes relatively low strength magnetic fields to generate low-field MRI imaging data of the patient, as compared to typical MRI imaging devices utilized in hospitals and imaging centers (which are generally in the range of 1.5 to 3 T (teslas)). In one example, the low-field MRI imaging device utilizes magnetic fields less than or equal to 0.1 T.

In one embodiment, the at least one low-field MRI quality assurance imaging data is of a prostate of the patient. However, the at least one low-field MRI quality assurance imaging data may be of any other anatomical object of the patient, such as, e.g., other organs, bones, lesions, or any other anatomical object of interest. The at least one low-field MRI quality assurance imaging data may comprise raw k-space data represented as an array of numbers representing spatial frequencies, MR fingerprinting data quantifying one or more properties of material or tissue, and/or reconstructed images generated from the raw k-space data (e.g., by applying the Fourier transform to the raw k-space data).

The at least one low-field MRI quality assurance imaging data may be received directly from the low-field MRI imaging device as the imaging data are acquired, or can be received by loading previously acquired imaging data from a storage or memory of a computer system or receiving imaging data that have been transmitted from a remote computer system.

At step 104, a quality assessment of a medical imaging analysis task is performed based on the at least one low-field MRI quality assurance imaging data using one or more machine learning based networks. The one or more machine learning based networks are trained during a prior offline training stage. Once trained, the one or more machine learning based networks are applied during an inference stage, e.g., to perform step 106.

The medical imaging analysis task is performed based on one or more low-field MRI diagnostic medical images of the patient. In one embodiment, the medical imaging analysis task comprises detection of cancer (e.g., prostate cancer). However, the medical imaging analysis task may be any other suitable medical imaging analysis task performed on the one or more low-field MRI diagnostic medical images, such as, e.g., anatomical landmark detection, segmentation, classification, etc. The medical imaging analysis task may be performed using any suitable approach. For example, detection of prostate cancer may be automatically performed using a machine learning based prostate cancer detection network. In one embodiment, the medical imaging analysis task is performed according to known approaches.

In one embodiment, the quality assessment is performed by detecting an incorrect position of the patient and image artifacts in the at least one low-field MRI quality assurance imaging data. The at least one low-field MRI quality assurance imaging data may be acquired prior to the acquisition of the one or more low-field MRI diagnostic medical images or at any other suitable time (e.g., after the acquisition of the one or more low-field MRI diagnostic medical images or between acquisitions of the one or more low-field MRI diagnostic medical images). In this embodiment, a machine learning based network is trained during the prior offline training stage to identify an incorrect positioning of the patient and image artifacts (e.g., due to metals in the patient, or patient wearables on the patient) in the at least one low-field MRI quality assurance imaging data. The machine learning based network may be trained according to a supervised approach or an unsupervised approach. In the supervised approach, low-field MRI training imaging data for a large cohort of individuals in various positions (e.g., postures) and configurations is acquired and the image quality of the training imaging data is labeled or scored manually. The machine learning based network is trained to classify the at least one low-field MRI quality assurance imaging data as being high quality or low quality based on the labeled training imaging data. In the unsupervised approach, a machine learning based out-of-distribution (OOD) detection network is trained to determine whether the at least one low-field MRI quality assurance imaging data is out of the distribution of the training data and thus not of a desired quality. The training of the OOD detection network does not require labels or diagnoses. In one embodiment, the OOD detection network comprises an autoencoder (or a variant of the autoencoder) architecture that memorizes key features of only the in-distribution data (i.e., training images of high quality). Images of low quality are assumed to have a significantly different distribution from the high-quality in-distribution images so that they can be identified by the autoencoder. The OOD detection network may be of any other suitable machine learning based architecture.

In one embodiment, the quality assessment is additionally or alternatively performed to detect motion of the patient during the acquisition of the one or more low-field MRI diagnostic imaging data. In this embodiment, the at least one low-field MRI quality assurance data comprises first low-field MRI quality assurance data and second low-field MRI quality assurance data. The first and second low-field MRI quality assurance data are acquired at different times. For example, the first low-field MRI quality assurance data may be acquired prior to the acquisition of the one or more low-field MRI diagnostic medical images and the second low-field MRI quality assurance data may be acquired after the acquisition of the one or more low-field MRI diagnostic imaging data. A machine learning based network is trained during the prior offline training stage to compare the first and second low-field MRI quality assurance imaging data to determine if the patient remained static. In one embodiment, the machine learning based network is implemented as a Siamese neural network for improved feature extraction for image similarity comparison. An exemplary framework for training a Siamese network for comparing the first and second low-field MRI quality assurance imaging data is shown in FIG. 2.

Figure 2:
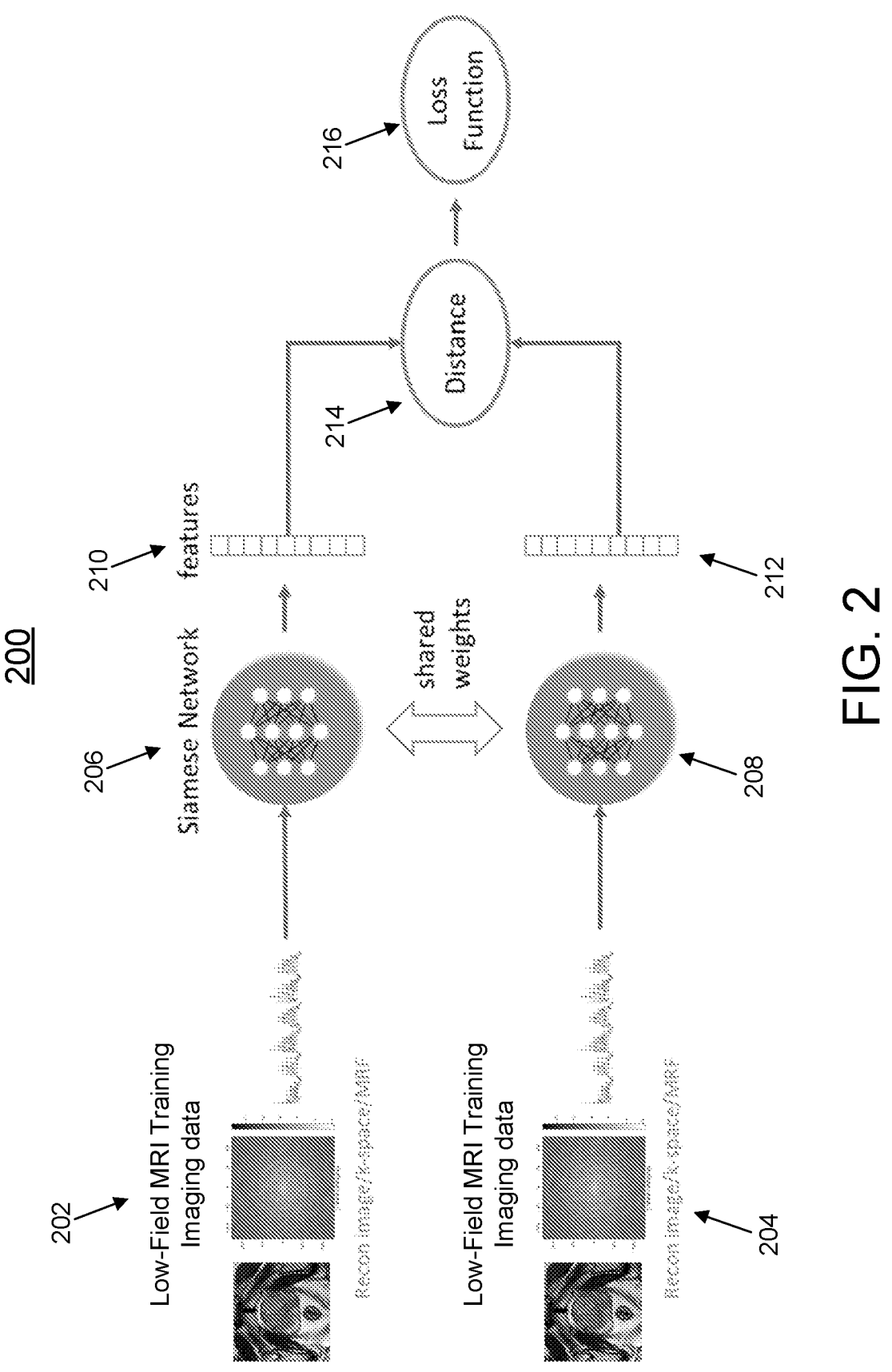
FIG. 2 shows a framework for training a Siamese network for comparing first and second low-field MRI quality assurance imaging data, in accordance with one or more embodiments.

FIG. 2 shows a framework 200 for training a Siamese network for comparing first and second low-field MRI quality assurance imaging data, in accordance with one or more embodiments. The steps of framework 200 are performed during a prior offline training stage to train the Siamese network. Once trained, the Siamese network may be applied during an online inference stage, such as, e.g., at step 106 of FIG. 1.

The Siamese network is trained with a pair of low-field MRI training imaging data 202 and 204, which may comprise raw k-space data, MR fingerprinting data, and/or reconstructed images. The Siamese network comprises two identical subnetworks 206 and 208 with the same architecture and parameters (i.e., shared weights). Each Siamese subnetwork 206 and 208 respectively receives low-field MRI training imaging data 202 and 204 as input and extracts features 210 and 212 as output. Siamese subnetworks 206 and 208 may be implemented using a CNN (convolutional neural network) for extracting features 210 and 212. Different types of CNNs, such as, e.g., ResNet or DenseNet, may be used based on the size of the training data. If reconstructed images of low-field MRI training imaging data 202 and 204 are not obtained, other types of networks (e.g., Transformer networks) may be used to extract features directly from the raw k-space data. A distance or similarity 214 between the features 210 and 212 may be calculated according to various distance functions, such as, e.g., Euclidian distance or cosine similarity. The Siamese network is trained according to loss function 216. In one example, loss function 216 may be a Triplet loss function as defined in Equation (1):

$$\mathcal{L}_{(A,P,N)}=\max(\mathcal{D}_{(A,P)}-\mathcal{D}_{(A,N)}+\alpha,0) \qquad (1)$$

where A is an anchor (reference) image/measurement, P is a positive example (another image/measurement from the same patient without motion), and N is a negative example (an image/measurement from another case or from the same case but with image quality issues). The Siamese network is trained to search for the best model that results in the distance between the encoded features of the anchor A and the positive example P to be less than or equal to the distance between the encoded features of the anchor A and the negative example N.

At step 106 of FIG. 1, results of the quality assessment are output. For example, the results of the quality assessment can be output by displaying the results of the quality assessment on a display device of a computer system, storing the results of the quality assessment on a memory or storage of a computer system, or by transmitting the results of the quality assessment to a remote computer system.

In one embodiment, where the results of the quality assessment indicate that the results of the medical imaging analysis task may not be accurate (e.g., due to incorrect patient posture, image artifacts, patient motion), a notification (e.g., sound or display prompt) may be presented to the user. The notification may prompt the user to reacquire the one or more low-field MRI diagnostic medical images to repeat the performance of the medical imaging analysis task.

In one embodiment, method 100 of FIG. 1 may be performed by a low-field MRI diagnostic system. The low-field MRI diagnostic system may comprise a low-field MRI image acquisition device and one or more computing devices (e.g., computer 702 of FIG. 7) for performing the steps of method 100 of FIG. 1. The low-field MRI diagnostic system may be installed as a kiosk in a pharmacy, a medical clinic, or any other publicly accessible area to enable the patient to acquire the low-field MRI diagnostic images him or herself for automatically performing medical imaging analysis task (e.g., detection of prostate cancer) of the low-field MRI diagnostic images. Advantageously, a quality assessment of the medical imaging analysis task is performed (e.g., according to method 100 of FIG. 1) to, e.g., notify the patient that the results of the medical imaging analysis task may not be accurate and prompt the patient to reacquire the low-field MRI diagnostic image to reperform the medical imaging analysis task. The quality assessment thus enables the automatic workflow for performing the medical imaging analysis task using the low-field MRI diagnostic system without requiring guidance, review, or intervention by a radiologist or other clinician. An exemplary workflow for the automatic detection of prostate cancer using a low-field MRI diagnostic system is shown in FIGS. 3 and 4.

FIG. 3 shows a workflow 300 for the automatic detection of prostate cancer using a low-field MRI diagnostic system, in accordance with one or more embodiments. While workflow 300 is performed for the automatic detection of prostate cancer, workflow 300 may be performed for any other medical imaging analysis task.

At step 302, a patient is positioned in a low-field MRI imaging device. The patient may be positioned in a contoured seat to limit patient position variability.

At step 304, a first quality assurance (Q/A) scan is acquired. The first quality assurance scan is acquired before acquisition of all other diagnostic images and measurements in workflow 300 (i.e., prostate gland localization scan acquired at step 306 of FIG. 3, and the cancer detection scan acquired at step 310 of FIG. 3). The acquisition of the first quality assurance scan may be performed very quickly since it is not required to include diagnostic information. Thus, the spatial resolution of the first quality assurance scan may be relatively low, no contrast is required within the prostate gland, and image reconstruction is not necessarily performed.

At step 306, a prostate gland localization scan is acquired. The prostate gland localization scan is targeted to localize the prostate gland and to measure gland volume. The prostate gland localization scan may be a T2 weighted sequence or a DWI (diffusion-weighted imaging) image with low b-value sequence to estimate the gland volume.

At step 308, the prostate gland localization scan is processed. In one embodiment, an AI (artificial intelligence) system may infer the prostate gland bounding box (i.e., an imaginary rectangle that serves as points of reference), a gland mask (i.e., a precise contour of the gland), or gland volume from the prostate gland localization scan from either the raw k-space or from reconstructed images.

In one embodiment, T2 or DWI with low b-value scans may be used for prostate gland localization. A segmentation network, implemented as, e.g., a U-Net or s similar architecture, may be applied to calculate the gland segmentation. The segmentation network receives as input reconstructed images with relatively high spatial resolution. If multiple sequences are used (e.g., T2 or DWI), the segmentation network can be applied on different sequences and a Dice coefficient between the segmentations is calculated. If the Dice coefficient is significantly less than 1 (e.g., <0.8), this suggests significant inter-contrast motion which may impact the cancer detection.

At step 310, a cancer detection scan is acquired based on the processed prostate gland localization scan. The cancer detection scan is targeted to detect abnormalities in the prostate gland an assess the malignancy risk.

At step 312, in one embodiment, a second quality assurance scan is acquired. The second quality assurance scan is acquired after acquisition of all other diagnostic images and measurements in workflow 300 (i.e., prostate gland localization scan acquired at step 306 of FIG. 3, and the cancer detection scan acquired at step 310 of FIG. 3).

At step 314, the cancer detection scan is processed to detect cancer in the cancer detection scan and determine a malignancy risk score 316. An AI system may be implemented to infer the risk score 316 correlated with whole prostate gland abnormality (and malignancy risk) computed from an acquisition signal limited to the gland area. The risk score 316 may be computed based on the raw signal (e.g., the k-space or MRF (magnetic resonance fingerprints)) or reconstructed images at various spatial resolution.

At step 318, a measurement quality assessment is performed based on one or more of the first quality assurance scan (acquired at step 304) and/or the second quality assurance scan (acquired at step 312). In one example, the measurement quality assessment is performed according to method 100 of FIG. 1. In one embodiment, the measurement quality assessment may be performed using only one of the first quality assurance scan (acquired at step 304) or the second quality assurance scan (acquired at step 312) to detection incorrect position of the patient (positioned at step 302) and image artifacts. In another embodiment, the measurement quality assessment may additionally or alternatively be performed using both the first quality assurance scan (acquired at step 304) and the second quality assurance scan (acquired at step 312) to identify significant patient movement during the acquisition of the diagnostic scans/measurements that may impact the cancer detection. This comparison may be performed in the image space or the raw data space, so that image reconstruction is optional.

In one embodiment, the at least one low-field MRI quality assurance imaging data received at step 102 of FIG. 1 may comprise one or more additional low-field MRI quality assurance imaging data, in addition to the first low-field MRI quality assurance imaging data and the second low-field MRI quality assurance imaging data. For example, additional low-field MRI quality assurance imaging data may be acquired after acquisition of some or all diagnostic images (e.g., localization scans, detection scans, etc.) for continuous monitoring of patient movement. An exemplary workflow for the automatic detection of prostate cancer using a low-field MRI diagnostic system using additional low-field MRI quality assurance imaging data is shown in FIG. 4.

FIG. 4 shows a workflow 400 for the automatic detection of prostate cancer using a low-field MRI diagnostic system based on additional low-field MRI quality assurance imaging data, in accordance with one or more embodiments. Workflow 400 of FIG. 4 is similar to workflow 300 of FIG. 3 but incorporates the acquisition of additional low-field MRI quality assurance imaging data. As shown in FIG. 4, workflow 400 includes step 402 where an additional quality assurance scan is acquired between the first quality assurance scan (acquired at step 304) and the second quality assurance scan (acquired at step 312). The additional quality assurance scan is acquired after the prostate gland localization scan is acquired (at step 306) but before the cancer detection scan is acquired (at step 310). Advantageously, the additional quality assurance scan enables continuous monitoring of patient movement. This ensures that the entire imaging protocol is not discarded because there is motion somewhere between the beginning and end. For example, if there is patient motion detected between the additional quality assurance scan (acquired at step 402) and the second quality assurance scan (acquired at step 312), the prostate gland localization scan (acquired at step 306) and the process (performed at step 308) may be retained and only the cancer detection scan acquisition step 310 and cancer detection scan process step 314 are reperformed.

To perform the quality assessment based on the first low-field MRI quality assurance imaging data, the second low-field MRI quality assurance imaging data, and the one or more additional low-field MRI quality assurance imaging data, the Siamese network may be utilized in real time to compare each consecutive pair (e.g., to compare the first quality assurance scan acquired at step 304 with the additional quality assurance scan acquired at step 402 and to compare the additional quality assurance scan acquired at step 402 with the second quality assurance scan acquired at step 312) or to compare the first quality assurance scan with each subsequent quality assurance scans (e.g., to compare the first quality assurance scan acquired at step 304 with the additional quality assurance scan acquired at step 402 and to compare the first quality assurance scan acquired at step 304 with the additional quality assurance scan acquired at step 402).

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

FIG. 5 shows an embodiment of an artificial neural network 500, in accordance with one or more embodiments. Alternative terms for "artificial neural network" are "neural network", "artificial neural net" or "neural net". Machine learning networks described herein, such as, e.g., the one or more machine learning based networks utilized at step 106 of FIG. 1 and subnetworks 206 and 208 of the Siamese network of FIG. 2, may be implemented using artificial neural network 500.

The artificial neural network 500 comprises nodes 502-522 and edges 532, 534, . . . , 536, wherein each edge 532, 534, . . . , 536 is a directed connection from a first node 502-522 to a second node 502-522. In general, the first node 502-522 and the second node 502-522 are different nodes 502-522, it is also possible that the first node 502-522 and the second node 502-522 are identical. For example, in FIG. 5, the edge 532 is a directed connection from the node 502 to the node 506, and the edge 534 is a directed connection from the node 504 to the node 506. An edge 532, 534, . . . , 536 from a first node 502-522 to a second node 502-522 is also denoted as "ingoing edge" for the second node 502-522 and as "outgoing edge" for the first node 502-522.

In this embodiment, the nodes 502-522 of the artificial neural network 500 can be arranged in layers 524-530, wherein the layers can comprise an intrinsic order introduced by the edges 532, 534, . . . , 536 between the nodes 502-522. In particular, edges 532, 534, . . . , 536 can exist only between neighboring layers of nodes. In the embodiment shown in FIG. 5, there is an input layer 524 comprising only nodes 502 and 504 without an incoming edge, an output layer 530 comprising only node 522 without outgoing edges, and hidden layers 526, 528 in-between the input layer 524 and the output layer 530. In general, the number of hidden layers 526, 528 can be chosen arbitrarily. The number of nodes 502 and 504 within the input layer 524 usually relates to the number of input values of the neural network 500, and the number of nodes 522 within the output layer 530 usually relates to the number of output values of the neural network 500.

In particular, a (real) number can be assigned as a value to every node 502-522 of the neural network 500. Here, $x^{(n)}_i$ denotes the value of the i-th node 502-522 of the n-th layer 524-530. The values of the nodes 502-522 of the input layer 524 are equivalent to the input values of the neural network 500, the value of the node 522 of the output layer 530 is equivalent to the output value of the neural network 500. Furthermore, each edge 532, 534, . . . , 536 can comprise a weight being a real number, in particular, the weight is a real number within the interval [−1, 1] or within the interval [0, 1]. Here, $w^{(m,n)}_{i,j}$ denotes the weight of the edge between the i-th node 502-522 of the m-th layer 524-530 and the j-th node 502-522 of the n-th layer 524-530. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 502-522 of the (n+1)-th layer 524-530 can be calculated based on the values of the nodes 502-522 of the n-th layer 524-530 by $$x^{(n+1)}_j = f\left(\sum_i x^{(n)}_i \cdot w^{(n)}_{i,j}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 524 are given by the input of the neural network 500, wherein values of the first hidden layer 526 can be calculated based on the values of the input layer 524 of the neural network, wherein values of the second hidden layer 528 can be calculated based in the values of the first hidden layer 526, etc.

In order to set the values $w^{(m,n)}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left( \sum_k \delta^{(n+1)}_k \cdot w^{(n+1)}_{j,k} \right) \cdot f'\left( \sum_i x^{(n)}_i \cdot w^{(n)}_{i,j} \right)$$

based on $\delta^{(n+1)}_j$, if the (n+1)-th layer is not the output layer, and $$\delta^{(n)}_j = \left( x^{(n+1)}_k - t^{(n+1)}_j \right) \cdot f'\left( \sum_i x^{(n)}_i \cdot w^{(n)}_{i,j} \right)$$

if the (n+1)-th layer is the output layer 530, wherein f' is the first derivative of the activation function, and $y^{(n+1)}_j$ is the comparison training value for the j-th node of the output layer 530.

FIG. 6 shows a convolutional neural network 600, in accordance with one or more embodiments. Machine learning networks described herein, such as, e.g., the one or more machine learning based networks utilized at step 106 of FIG. 1 and subnetworks 206 and 208 of the Siamese network of FIG. 2, may be implemented using convolutional neural network 600.

In the embodiment shown in FIG. 6, the convolutional neural network comprises 600 an input layer 602, a convolutional layer 604, a pooling layer 606, a fully connected layer 608, and an output layer 610. Alternatively, the convolutional neural network 600 can comprise several convolutional layers 604, several pooling layers 606, and several fully connected layers 608, as well as other types of layers. The order of the layers can be chosen arbitrarily, usually fully connected layers 608 are used as the last layers before the output layer 610.

In particular, within a convolutional neural network 600, the nodes 612-620 of one layer 602-610 can be considered to be arranged as a d-dimensional matrix or as a d-dimensional image. In particular, in the two-dimensional case the value of the node 612-620 indexed with i and j in the n-th layer 602-610 can be denoted as $x^{(n)}_{[i,j]}$. However, the arrangement of the nodes 612-620 of one layer 602-610 does not have an effect on the calculations executed within the convolutional neural network 600 as such, since these are given solely by the structure and the weights of the edges.

In particular, a convolutional layer 604 is characterized by the structure and the weights of the incoming edges forming a convolution operation based on a certain number of kernels. In particular, the structure and the weights of the incoming edges are chosen such that the values $x^{(n)}_k$ of the nodes 614 of the convolutional layer 604 are calculated as a convolution $x^{(n)}_k = K_k * x^{(n-1)}$ based on the values $x^{(n-1)}$ of the nodes 612 of the preceding layer 602, where the convolution * is defined in the two-dimensional case as $$x^{(n)}_k[i, j] = (K_k * x^{(n-1)})[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 612-618 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 612-620 in the respective layer 602-610. In particular, for a convolutional layer 604, the number of nodes 614 in the convolutional layer is equivalent to the number of nodes 612 in the preceding layer 602 multiplied with the number of kernels.

If the nodes 612 of the preceding layer 602 are arranged as a d-dimensional matrix, using a plurality of kernels can be interpreted as adding a further dimension (denoted as "depth" dimension), so that the nodes 614 of the convolutional layer 604 are arranged as a (d+1)-dimensional matrix. If the nodes 612 of the preceding layer 602 are already arranged as a (d+1)-dimensional matrix comprising a depth dimension, using a plurality of kernels can be interpreted as expanding along the depth dimension, so that the nodes 614 of the convolutional layer 604 are arranged also as a (d+1)-dimensional matrix, wherein the size of the (d+1)-dimensional matrix with respect to the depth dimension is by a factor of the number of kernels larger than in the preceding layer 602.

The advantage of using convolutional layers 604 is that spatially local correlation of the input data can exploited by enforcing a local connectivity pattern between nodes of adjacent layers, in particular by each node being connected to only a small region of the nodes of the preceding layer.

In embodiment shown in FIG. 6, the input layer 602 comprises 36 nodes 612, arranged as a two-dimensional 6×6 matrix. The convolutional layer 604 comprises 72 nodes 614, arranged as two two-dimensional 6×6 matrices, each of the two matrices being the result of a convolution of the values of the input layer with a kernel. Equivalently, the nodes 614 of the convolutional layer 604 can be interpreted as arranges as a three-dimensional 6×6×2 matrix, wherein the last dimension is the depth dimension.

A pooling layer 606 can be characterized by the structure and the weights of the incoming edges and the activation function of its nodes 616 forming a pooling operation based on a non-linear pooling function f. For example, in the two dimensional case the values $x^{(n)}$ of the nodes 616 of the pooling layer 606 can be calculated based on the values $x^{(n-1)}$ of the nodes 614 of the preceding layer 604 as $$x^{(n)}[i,j] = f(x^{(n-1)}[id_1, jd_2], \dots, x^{(n-1)}[id_1 + d_1 - 1, jd_2 + d_2 - 1])$$

In other words, by using a pooling layer 606, the number of nodes 614, 616 can be reduced, by replacing a number d1·d2 of neighboring nodes 614 in the preceding layer 604 with a single node 616 being calculated as a function of the values of said number of neighboring nodes in the pooling layer. In particular, the pooling function f can be the max-function, the average or the L2-Norm. In particular, for a pooling layer 606 the weights of the incoming edges are fixed and are not modified by training.

The advantage of using a pooling layer 606 is that the number of nodes 614, 616 and the number of parameters is reduced. This leads to the amount of computation in the network being reduced and to a control of overfitting.

In the embodiment shown in FIG. 6, the pooling layer 606 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 608 can be characterized by the fact that a majority, in particular, all edges between nodes 616 of the previous layer 606 and the nodes 618 of the fully-connected layer 608 are present, and wherein the weight of each of the edges can be adjusted individually.

In this embodiment, the nodes 616 of the preceding layer 606 of the fully-connected layer 608 are displayed both as two-dimensional matrices, and additionally as non-related nodes (indicated as a line of nodes, wherein the number of nodes was reduced for a better presentability). In this embodiment, the number of nodes 618 in the fully connected layer 608 is equal to the number of nodes 616 in the preceding layer 606. Alternatively, the number of nodes 616, 618 can differ.

Furthermore, in this embodiment, the values of the nodes 620 of the output layer 610 are determined by applying the Softmax function onto the values of the nodes 618 of the preceding layer 608. By applying the Softmax function, the sum the values of all nodes 620 of the output layer 610 is 1, and all values of all nodes 620 of the output layer are real numbers between 0 and 1.

A convolutional neural network 600 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 600 can be trained based on the backpropagation algorithm. For preventing overfitting, methods of regularization can be used, e.g. dropout of nodes 612-620, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 3-4. Certain steps or functions of the methods and workflows described herein, including one or more of the steps or functions of FIG. 1 or 3-4, may be performed by a server or by another processor in a network-based cloud-computing system. Certain steps or functions of the methods and workflows described herein, including one or more of the steps of FIG. 1 or 3-4, may be performed by a client computer in a network-based cloud computing system. The steps or functions of the methods and workflows described herein, including one or more of the steps of FIG. 1 or 3-4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 3-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIG. 1 or 3-4 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIG. 1 or 3-4. Accordingly, by executing the computer program instructions, the processor 704 executes the method and workflow steps or functions of FIG. 1 or 3-4. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

An image acquisition device 714 can be connected to the computer 702 to input image data (e.g., medical images) to the computer 702. It is possible to implement the image acquisition device 714 and the computer 702 as one device. It is also possible that the image acquisition device 714 and the computer 702 communicate wirelessly through a network. In a possible embodiment, the computer 702 can be located remotely with respect to the image acquisition device 714.

Any or all of the systems and apparatus discussed herein may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving first and second low-field MRI (magnetic resonance imaging) quality assurance imaging data of a patient and low-field MRI diagnostic imaging data of the patient, the first low-field MRI quality assurance imaging data being acquired before acquisition of the low-field MRI diagnostic imaging data and the second low-field MRI quality assurance imaging data being acquired after acquisition of the low-field MRI diagnostic imaging data;
performing a medical imaging analysis task based on the low-field MRI diagnostic imaging data using a machine learning based network;
performing a quality assessment of the medical imaging analysis task to detect an incorrect position of the patient based on the first and the second low-field MRI quality assurance imaging data using one or more machine learning based networks, wherein at least one of the one or more machine learning based networks is trained to identify incorrect positions of patients in low-field MRI imaging data using training imaging data, the training imaging data depicting individuals in different positions and labelled to indicate image quality; and
outputting results of the quality assessment.

2. The computer-implemented method of claim 1, wherein performing a quality assessment of the medical imaging analysis task to detect an incorrect position of the patient based on the first and the second low-field MRI quality assurance imaging data using one or more machine learning based networks comprises:
performing the quality assessment of the medical imaging analysis task to further detect image artifacts based on at least one of the first or the second low-field MRI quality assurance imaging data using the one or more machine learning based networks.

3. The computer-implemented method of claim 1, wherein the at least one of the one or more machine learning based networks is trained with a supervised approach using the training imaging data to classify at least one of the first or the second low-field MRI quality assurance imaging data as being one of high quality or low quality.

4. The computer-implemented method of claim 2, wherein at least another one of the one or more machine learning based networks is trained with an unsupervised approach using unlabeled training data to determine whether the at least one of the first or the second low-field MRI quality assurance imaging data is out of distribution of the unlabeled training data.

5. The computer-implemented method of claim 1, wherein performing a quality assessment of the medical imaging analysis task to detect an incorrect position of the patient based on the first and the second low-field MRI quality assurance imaging data using one or more machine learning based networks comprises:
extracting a first set of features from the first low-field MRI quality assurance imaging data using the one or more machine learning based networks;

extracting a second set of features from the second low-field MRI quality assurance imaging data using the one or more machine learning based networks; and computing a distance between the first set of features and the second set of features.

6. The computer-implemented method of claim 5, wherein:

the one or more machine learning based networks comprise a Siamese neural network, extracting a first set of features from the first low-field MRI quality assurance imaging data using the one or more machine learning based networks comprises extracting the first set of features from the first low-field MRI quality assurance imaging data using a first subnetwork of the Siamese neural network, and extracting the second set of features from the second low-field MRI quality assurance imaging data comprises extracting the second set of features from the second low-field MRI quality assurance imaging data using a second subnetwork of the Siamese neural network.

7. The computer-implemented method of claim 1, further comprising receiving one or more additional low-field MRI quality assurance imaging data of the patient acquired between the first low-field MRI quality assurance imaging data and the second low-field MRI quality assurance imaging data, wherein performing a quality assessment of the medical imaging analysis task to detect an incorrect position of the patient based on the first and the second low-field MRI quality assurance imaging data using one or more machine learning based networks comprises:

performing the quality assessment based on the first low-field MRI quality assurance imaging data, the second low-field MRI quality assurance imaging data, and the one or more additional low-field MRI quality assurance imaging data.

8. The computer-implemented method of claim 1, wherein the first and the second low-field MRI quality assurance imaging data comprises at least one of raw k-space data, MR fingerprinting data, or reconstructed images.

9. An apparatus comprising:

means for receiving first and second low-field MRI (magnetic resonance imaging) quality assurance imaging data of a patient and low-field MRI diagnostic imaging data of the patient, the first low-field MRI quality assurance imaging data being acquired before acquisition of the low-field MRI diagnostic imaging data and the second low-field MRI quality assurance imaging data being acquired after acquisition of the low-field MRI diagnostic imaging data;

means for performing a medical imaging analysis task based on the low-field MRI diagnostic imaging data using a machine learning based network;

means for performing a quality assessment of the medical imaging analysis task to detect an incorrect position of the patient based on the first and the second low-field MRI quality assurance imaging data using one or more machine learning based networks, wherein at least one of the one or more machine learning based networks is trained to identify incorrect positions of patients in low-field MRI imaging data using training imaging data, the training imaging data depicting individuals in different positions and labelled to indicate image quality; and means for outputting results of the quality assessment.

10. The apparatus of claim 9, wherein the means for performing a quality assessment of the medical imaging analysis task to detect an incorrect position of the patient based on the first and the second low-field MRI quality assurance imaging data using one or more machine learning based networks comprises:

means for performing the quality assessment of the medical imaging analysis task to further detect image artifacts based on at least one of the first or the second low-field MRI quality assurance imaging data using the one or more machine learning based networks.

11. The apparatus of claim 9, wherein the at least one of the one or more machine learning based networks is trained with a supervised approach using the training imaging data to classify at least one of the first or the second low-field MRI quality assurance imaging data as being one of high quality or low quality.

12. The apparatus of claim 10, wherein at least another one of the one or more machine learning based networks is trained with an unsupervised approach using unlabeled training data to determine whether the at least one of the first or the second low-field MRI quality assurance imaging data is out of distribution of the unlabeled training data.

13. A non-transitory computer readable medium storing computer program instructions, the computer program instructions when executed by a processor cause the processor to perform operations comprising:

receiving first and second low-field MRI (magnetic resonance imaging) quality assurance imaging data of a patient and low-field MRI diagnostic imaging data of the patient, the first low-field MRI quality assurance imaging data being acquired before acquisition of the low-field MRI diagnostic imaging data and the second low-field MRI quality assurance imaging data being acquired after acquisition of the low-field MRI diagnostic imaging data;

performing a medical imaging analysis task based on the low-field MRI diagnostic imaging data using a machine learning based network;

performing a quality assessment of the medical imaging analysis task to detect an incorrect position of the patient based on the first and the second low-field MRI quality assurance imaging data using one or more machine learning based networks, wherein at least one of the one or more machine learning based networks is trained to identify incorrect positions of patients in low-field MRI imaging data using training imaging data, the training imaging data depicting individuals in different positions and labelled to indicate image quality; and outputting results of the quality assessment.

14. The non-transitory computer readable medium of claim 13, wherein performing a quality assessment of the medical imaging analysis task to detect an incorrect position of the patient based on the first and the second low-field MRI quality assurance imaging data using one or more machine learning based networks comprises:

performing the quality assessment of the medical imaging analysis task to further detect image artifacts based on at least one of the first or the second low-field MRI quality assurance imaging data using the one or more machine learning based networks.

15. The non-transitory computer readable medium of claim 13, wherein performing a quality assessment of the medical imaging analysis task to detect an incorrect position of the patient based on the first and the second low-field MRI quality assurance imaging data using one or more machine learning based networks comprises:

extracting a first set of features from the first low-field MRI quality assurance imaging data using the one or more machine learning based networks;

extracting a second set of features from the second low-field MRI quality assurance imaging data using the one or more machine learning based networks; and computing a distance between the first set of features and the second set of features.

16. The non-transitory computer readable medium of claim 15, wherein:

the one or more machine learning based networks comprise a Siamese neural network, extracting a first set of features from the first low-field MRI quality assurance imaging data using the one or more machine learning based networks comprises extracting the first set of features from the first low-field MRI quality assurance imaging data using a first subnetwork of the Siamese neural network, and extracting the second set of features from the second low-field MRI quality assurance imaging data comprises extracting the second set of features from the second low-field MRI quality assurance imaging data using a second subnetwork of the Siamese neural network.

17. The non-transitory computer readable medium of claim 13, the operations further comprising receiving one or more additional low-field MRI quality assurance imaging data of the patient acquired between the first low-field MRI quality assurance imaging data and the second low-field MRI quality assurance imaging data, wherein performing a quality assessment of the medical imaging analysis task to detect an incorrect position of the patient based on the first and the second low-field MRI quality assurance imaging data using one or more machine learning based networks comprises:

performing the quality assessment based on the first low-field MRI quality assurance imaging data, the second low-field MRI quality assurance imaging data, and the one or more additional low-field MRI quality assurance imaging data.

* * * * *